United States Patent
Biedermann et al.

(10) Patent No.: US 9,445,847 B2
(45) Date of Patent: Sep. 20, 2016

(54) POLYAXIAL BONE ANCHORING DEVICE

(71) Applicant: Biedermann Technologies GmbH & Co. KG, Donaueschingen (DE)

(72) Inventors: Lutz Biedermann, VS-Villingen (DE); Wilfried Matthis, Weisweil (DE)

(73) Assignee: Biedermann Technologies GmbH & Co. KG, Donaueschingen (DE)

( * ) Notice: Subject to any disclaimer, the term of this patent is extended or adjusted under 35 U.S.C. 154(b) by 0 days.

(21) Appl. No.: 13/720,775

(22) Filed: Dec. 19, 2012

(65) Prior Publication Data
US 2013/0165977 A1    Jun. 27, 2013

Related U.S. Application Data

(60) Provisional application No. 61/580,012, filed on Dec. 23, 2011.

(30) Foreign Application Priority Data

Dec. 23, 2011    (EP) .................................... 11195714

(51) Int. Cl.
  *A61B 17/70*    (2006.01)
(52) U.S. Cl.
  CPC ....... *A61B 17/7037* (2013.01); *A61B 17/7032* (2013.01); *A61B 17/7035* (2013.01)
(58) Field of Classification Search
  CPC .................................. A61B 17/7032–17/7046
  USPC .................. 606/246, 264–265, 300–321
  See application file for complete search history.

(56) References Cited

U.S. PATENT DOCUMENTS

| | | | |
|---|---|---|---|
| 6,010,503 A | 1/2000 | Richelsoph et al. | |
| 6,355,040 B1 * | 3/2002 | Richelsoph et al. | 606/272 |
| 6,835,196 B2 * | 12/2004 | Biedermann et al. | 606/308 |

(Continued)

FOREIGN PATENT DOCUMENTS

| | | |
|---|---|---|
| CN | 101810510 A | 8/2010 |
| CN | 102202589 A | 9/2011 |

(Continued)

OTHER PUBLICATIONS

Extended European Search Report for European Application No. 11195714.8, extended European Search Report dated May 4, 2012 and mailed May 11, 2012 (7 pgs.).

*Primary Examiner* — Eduardo C Robert
*Assistant Examiner* — Michelle C Eckman
(74) *Attorney, Agent, or Firm* — Lewis Roca Rothgerber Christie LLP

(57) ABSTRACT

A polyaxial bone anchoring device includes an anchoring element having a shank and a head having an outer surface portion shaped as a segment of a sphere, a receiving part having a seat portion for receiving the head, and a pressure element having a head contacting surface portion having at least two circumferentially distinct projections and defining a recess for holding the head, the recess having a first region configured to receive the head and a second region defined by at least part of one of the projections and having an undersize compared to the shape of the head, such that when the head is held in the recess, the projections extend over a portion of the head with the largest outer diameter, and the head contacting surface portion corresponding to the second region is expanded from a neutral position to clamp the head by friction.

21 Claims, 5 Drawing Sheets

(56) References Cited

U.S. PATENT DOCUMENTS

| | | | |
|---|---|---|---|
| 7,682,377 B2* | 3/2010 | Konieczynski et al. | 606/269 |
| 7,749,258 B2* | 7/2010 | Biedermann et al. | 606/308 |
| 7,828,829 B2* | 11/2010 | Ensign | 606/305 |
| 7,951,172 B2* | 5/2011 | Chao et al. | 606/265 |
| 8,048,133 B2* | 11/2011 | Biedermann et al. | 606/308 |
| 8,075,603 B2* | 12/2011 | Hammill et al. | 606/308 |
| 8,083,776 B2* | 12/2011 | Alvarez | 606/265 |
| 8,088,152 B2* | 1/2012 | Schumacher | 606/328 |
| 8,100,946 B2* | 1/2012 | Strausbaugh et al. | 606/266 |
| 8,157,846 B2* | 4/2012 | Randol et al. | 606/279 |
| 8,221,472 B2* | 7/2012 | Peterson et al. | 606/270 |
| 8,313,516 B2* | 11/2012 | Konieczynski et al. | 606/266 |
| 8,382,809 B2* | 2/2013 | Kaufman et al. | 606/305 |
| 8,419,778 B2* | 4/2013 | Barry | 606/308 |
| 8,444,681 B2* | 5/2013 | Jackson et al. | 606/300 |
| 8,506,601 B2* | 8/2013 | Gephart et al. | 606/266 |
| 8,506,611 B2* | 8/2013 | Biedermann et al. | 606/308 |
| 8,628,558 B2* | 1/2014 | Harvey et al. | 606/267 |
| 8,632,571 B2* | 1/2014 | Kraus | 606/264 |
| 8,641,737 B2* | 2/2014 | Matthis et al. | 606/265 |
| 9,333,011 B2 | 5/2016 | Biedermann et al. | |
| 2002/0133154 A1 | 9/2002 | Saint Martin | |
| 2004/0153077 A1* | 8/2004 | Biedermann et al. | 606/73 |
| 2004/0267264 A1* | 12/2004 | Konieczynski et al. | 606/73 |
| 2005/0154393 A1* | 7/2005 | Doherty et al. | 606/73 |
| 2005/0159750 A1* | 7/2005 | Doherty | 606/73 |
| 2005/0203516 A1* | 9/2005 | Biedermann et al. | 606/61 |
| 2006/0195098 A1* | 8/2006 | Schumacher | 606/61 |
| 2006/0200131 A1* | 9/2006 | Chao et al. | 606/61 |
| 2006/0241599 A1* | 10/2006 | Konieczynski et al. | 606/61 |
| 2007/0118123 A1* | 5/2007 | Strausbaugh et al. | 606/61 |
| 2009/0105770 A1* | 4/2009 | Berrevoets et al. | 606/308 |
| 2009/0198280 A1* | 8/2009 | Spratt et al. | 606/267 |
| 2009/0216280 A1* | 8/2009 | Hutchinson | 606/279 |
| 2010/0023061 A1* | 1/2010 | Randol et al. | 606/278 |
| 2010/0145394 A1* | 6/2010 | Harvey et al. | 606/302 |
| 2010/0152787 A1* | 6/2010 | Walsh et al. | 606/308 |
| 2010/0160980 A1* | 6/2010 | Walsh et al. | 606/308 |
| 2010/0198272 A1* | 8/2010 | Keyer et al. | 606/302 |
| 2010/0228293 A1 | 9/2010 | Courtney et al. | |
| 2010/0234902 A1* | 9/2010 | Biedermann et al. | 606/305 |
| 2010/0318135 A1* | 12/2010 | Biedermann et al. | 606/305 |
| 2010/0324599 A1* | 12/2010 | Montello et al. | 606/264 |
| 2011/0066189 A2* | 3/2011 | Biedermann et al. | 606/301 |
| 2011/0106166 A1* | 5/2011 | Keyer et al. | 606/264 |
| 2011/0112578 A1* | 5/2011 | Keiser et al. | 606/264 |
| 2011/0196430 A1 | 8/2011 | Walsh et al. | |
| 2011/0213424 A1* | 9/2011 | Biedermann et al. | 606/305 |
| 2012/0041490 A1* | 2/2012 | Jacob et al. | 606/264 |
| 2012/0041495 A9* | 2/2012 | Biedermann et al. | 606/305 |
| 2012/0089194 A1* | 4/2012 | Strausbaugh et al. | 606/301 |
| 2012/0095516 A1* | 4/2012 | Dikeman | 606/305 |
| 2012/0101532 A1* | 4/2012 | Biedermann et al. | 606/305 |
| 2012/0143260 A1* | 6/2012 | Gunn | A61B 17/7037 606/302 |
| 2012/0143262 A1* | 6/2012 | Jensen et al. | 606/304 |
| 2012/0165882 A1* | 6/2012 | Biedermann | A61B 17/7037 606/328 |
| 2012/0179209 A1* | 7/2012 | Biedermann et al. | 606/305 |
| 2012/0179210 A1* | 7/2012 | Garamszegi | 606/305 |
| 2012/0277806 A1* | 11/2012 | Smith et al. | 606/308 |
| 2013/0046345 A1* | 2/2013 | Jones et al. | 606/266 |
| 2013/0053890 A1* | 2/2013 | Elshihabi | 606/261 |
| 2013/0066376 A1* | 3/2013 | Biedermann et al. | 606/278 |
| 2013/0096618 A1* | 4/2013 | Chandanson et al. | 606/278 |
| 2013/0172937 A1* | 7/2013 | Davenport et al. | 606/278 |
| 2013/0197586 A1* | 8/2013 | Matthis et al. | 606/278 |
| 2013/0226243 A1* | 8/2013 | Kraus | 606/264 |
| 2013/0268006 A1* | 10/2013 | Garamszegi | 606/266 |
| 2013/0345756 A1* | 12/2013 | Berrevoets et al. | 606/278 |
| 2014/0031880 A1* | 1/2014 | Biedermann et al. | 606/305 |
| 2014/0046374 A1* | 2/2014 | Asaad et al. | 606/267 |
| 2014/0163619 A1 | 6/2014 | Harvey et al. | |

FOREIGN PATENT DOCUMENTS

| | | |
|---|---|---|
| JP | 11-318933 A | 11/1999 |
| JP | 2002-315756 A | 10/2002 |

* cited by examiner

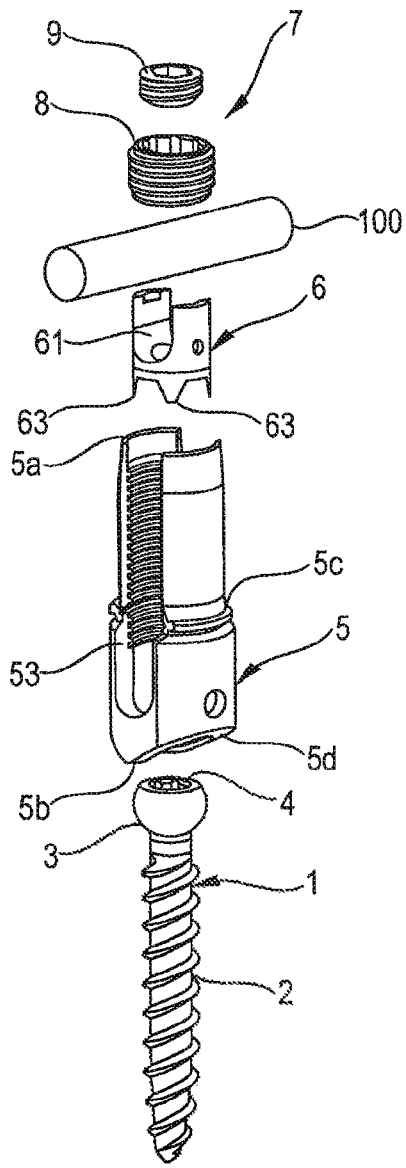
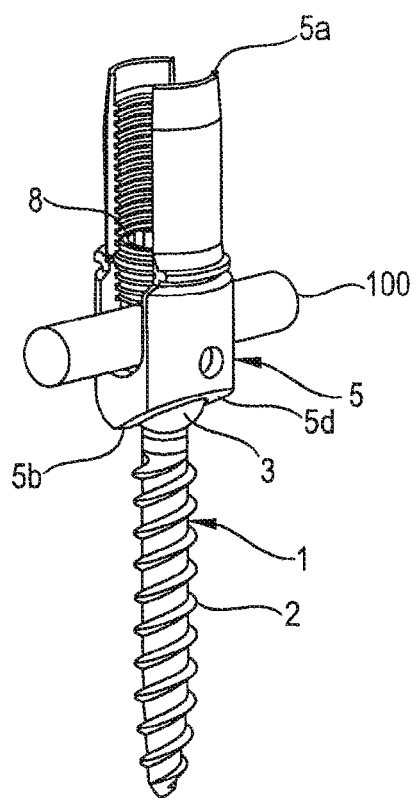
Fig. 1
Fig. 2

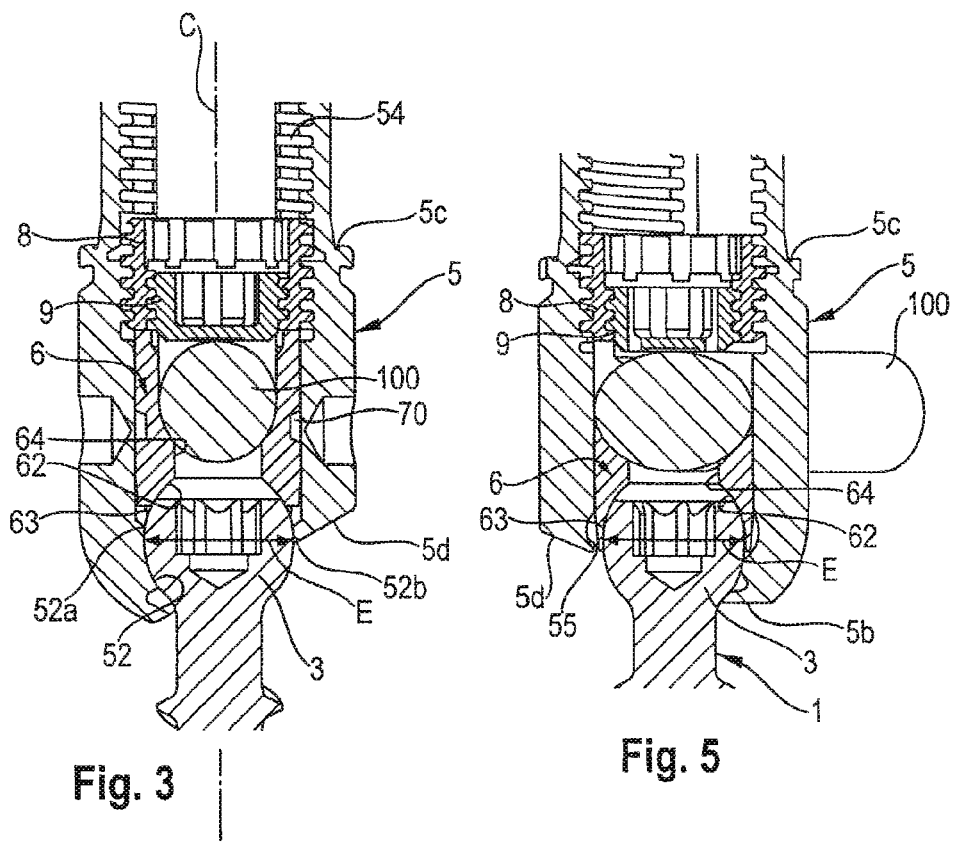
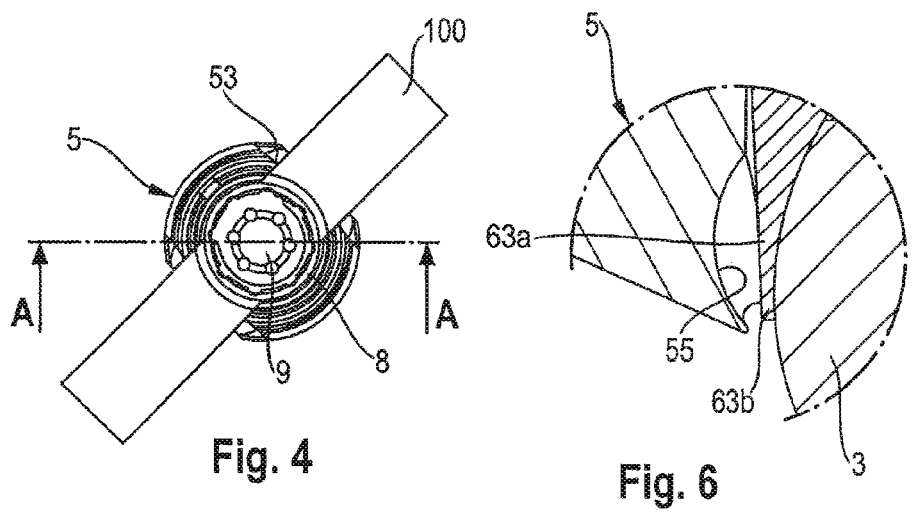
Fig. 3   Fig. 5   Fig. 4   Fig. 6

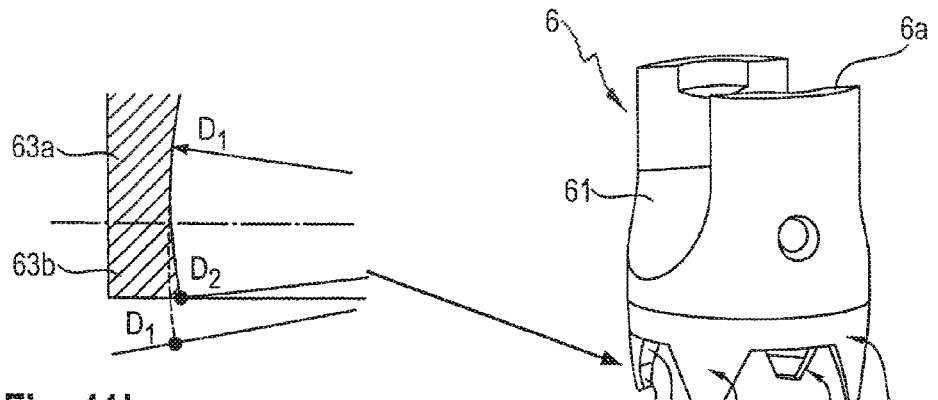
Fig. 11b
Fig. 11a
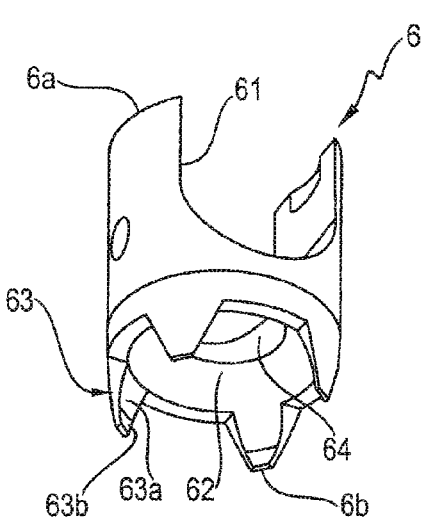
Fig. 12
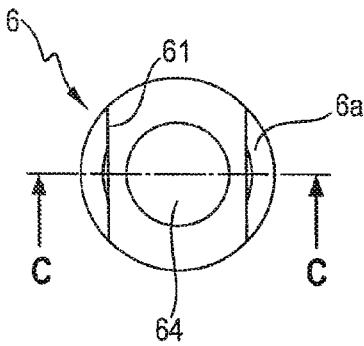
Fig. 13
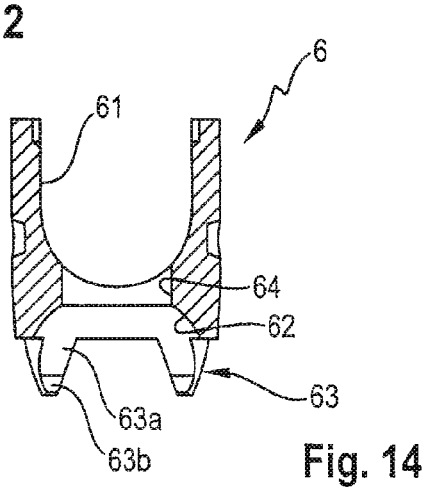
Fig. 14

POLYAXIAL BONE ANCHORING DEVICE

CROSS-REFERENCE TO RELATED APPLICATION(S)

The present application claims the benefit of U.S. Provisional Patent Application Ser. No. 61/580,012, filed Dec. 23, 2011, the contents of which are hereby incorporated by reference in their entirety, and claims priority to European Patent Application EP 11 195 714.8, filed Dec. 23, 2011, the contents of which are hereby incorporated by reference in their entirety.

BACKGROUND

1. Field of the Invention

The invention relates to a polyaxial bone anchoring device for anchoring a stabilization rod to bones or vertebrae. The bone anchoring device includes an anchoring element, a receiving part for receiving a head of the bone anchoring element and for receiving a stabilization rod to be connected to the anchoring element. The anchoring element is pivotably held in a seat in the receiving part, and can be fixed at an angle relative to the receiving part by exerting pressure onto the head via a pressure element which is arranged in the receiving part. The anchoring element may have a head with a spherical outer surface portion including a largest outer diameter, and the pressure element may include a head contacting surface portion including at least two circumferentially distinct lugs extending along a region including the largest outer diameter of the head when the pressure element is placed onto the head. The pressure element may have an undersize or be undersized in a region of the lugs corresponding to the head, such that the head is clamped by friction between the head and the lugs, causing the anchoring element to be maintained at a desired temporary angular position before final locking of the head.

2. Description of Related Art

US 2004/0267264 A1 describes a polyaxial fixation device wherein the polyaxial bone screw includes an engagement member that is adapted to provide sufficient friction between the spherical head and the receiver member to enable the shank to be maintained in a desired angular orientation before locking the spherical head within the receiver member. The engagement member is realized, for example, by an open snap ring around the head or by spring members provided at the compression cap to frictionally engage the spherical head or by a slot provided in the compression cap.

SUMMARY

It is an object of the invention to provide a bone anchoring device which allows for improved handling during surgery, while ensuring safe fixation and which is at the same time simple to manufacture.

With the bone anchoring device according to embodiments of the invention, a slight clamping of a head of a bone anchoring element in a desired angular position with respect to a receiving part, without locking the head, can be achieved. This allows maintaining of the receiving part in an adjustable angular position relative to the bone anchoring element. In this condition, the pressure element exerts a preload onto the head where the head is not locked, but is prevented from freely pivoting. When the head is temporarily clamped, alignment of the receiving part with respect to a rod and the insertion of the rod is more easily facilitated, in particular in a situation in which a plurality of bone anchors have to be connected to the rod. Furthermore, when the rod is already inserted into the receiving parts, adjustments of the rod are still possible without completely loosening the respective heads.

An amount of preload exerted onto the head by the pressure element can be exactly predefined by dimensioning the size of the pressure element with respect to the head, in view of the desired friction force between the pressure element and the head.

The bone anchoring device is simple to manufacture and adaptable to, for example, tolerances between the head, the receiving part, and the pressure element with respect to each other.

DESCRIPTION OF THE DRAWINGS

Further features and advantages of the invention will become apparent from the description of embodiments by means of the accompanying drawings. In the drawings:

FIG. 1 shows an exploded perspective view of a polyaxial bone anchoring device according to a first embodiment;

FIG. 2 shows a perspective view of the bone anchoring device of FIG. 1 in an assembled state;

FIG. 3 shows a cross-sectional view of the polyaxial bone anchoring device of FIGS. 1 and 2 in the assembled state, the cross-section being taken in a plane perpendicular to an axis of an inserted rod;

FIG. 4 shows a top view of the bone anchoring device of FIGS. 1 and 2;

FIG. 5 shows a cross-sectional view of the bone anchoring device of FIG. 1 and in the assembled state, the cross-section taken along line A-A in FIG. 4;

FIG. 6 shows an enlarged view of a portion of FIG. 5;

FIG. 11a shows a perspective view from a side of a pressure element according to the first embodiment;

FIG. 11b shows an enlarged portion of FIG. 11a;

FIG. 12 shows a perspective view of the pressure element of FIG. 11a;

FIG. 13, shows a top view of the pressure element of FIG. 11a;

FIG. 14 shows a cross-sectional view of the pressure element of FIG. 11a, the cross-section along line C-C in FIG. 13;

DETAILED DESCRIPTION

Figure 7:
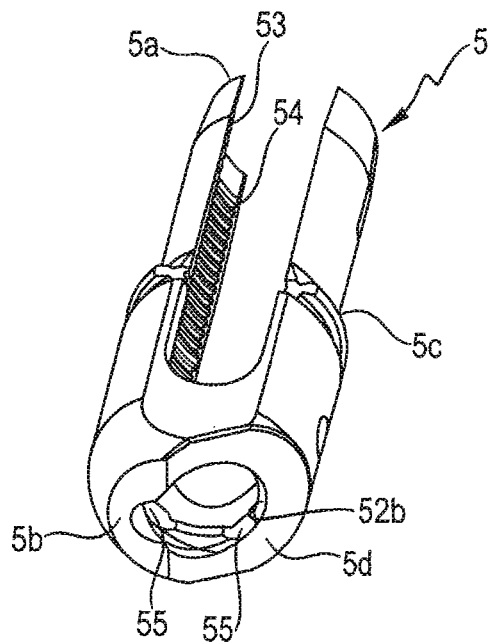
FIG. 7 shows a perspective view of the receiving part of the polyaxial bone anchoring device according to the first embodiment.
Figure 8:
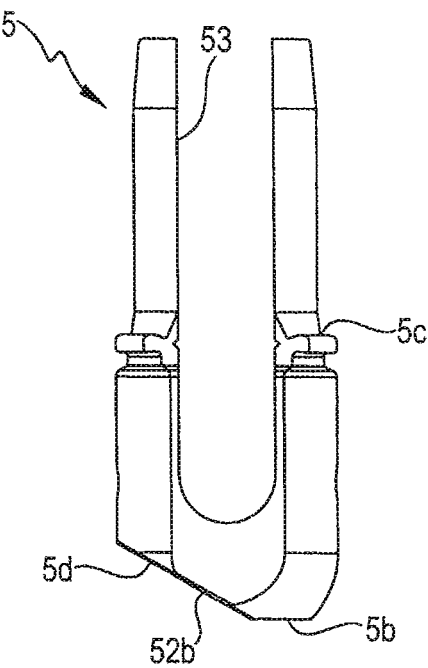
FIG. 8 shows a side view of the receiving part of FIG. 7.
Figure 9:
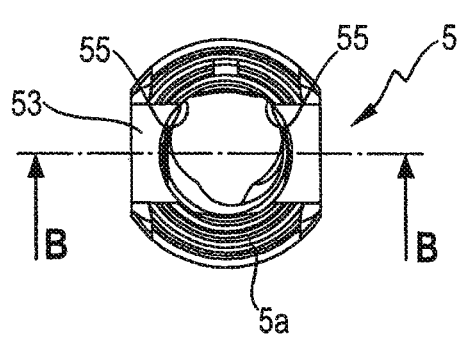
FIG. 9 shows a top view of the receiving part of FIG. 7.
Figure 10:
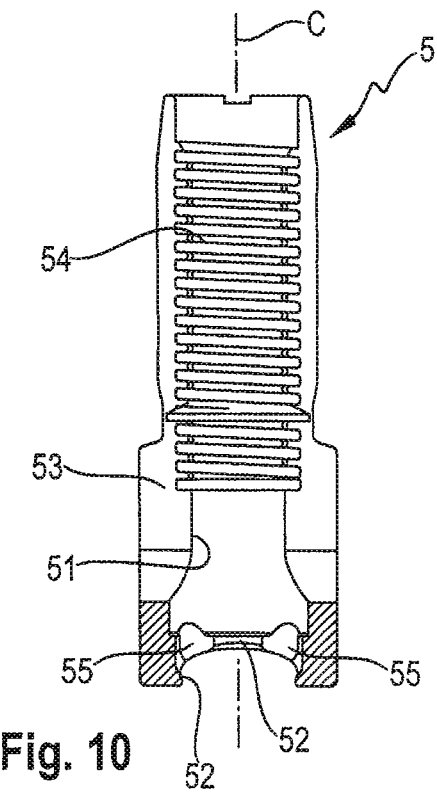
FIG. 10 shows a cross-sectional view of the receiving part of FIG. 7, the cross-section being taken along line B-B in FIG. 9.

A polyaxial bone anchoring device according to a first embodiment, which is generally shown in FIGS. 1 and 2, includes a bone anchoring element 1 in the form of a screw member having a threaded shank 2 and a head 3. The head 3 is shaped as a spherical segment that has a size including an equator or largest diameter E (see, e.g., FIG. 3). On its free end, the head 3 has a recess 4 for engagement with a tool. The bone anchoring device further includes a receiving part 5 for connecting the screw member 1 to a rod 100. A pressure element 6 is arranged in the receiving part on top of the head 3. For securing the rod 100 in the receiving part 5 and for exerting pressure onto the head 3, a locking device 7 in the form of, for example, an outer locking element 8 which cooperates with the receiving part 5 and an inner locking element 9 cooperating with the outer locking element 8 are provided.

As shown in particular in FIGS. 3 to 10, the receiving part 5 is substantially cylindrical and has a top end 5a, a bottom end 5b, and a bore 51 extending from the top end 5a towards the bottom end 5b, the bore having a bore axis C. At the bottom end 5b, a seat portion 52 is provided for accommodating the head 3. The seat portion 52 is spherically-shaped with a radius corresponding substantially to a radius of the head 3, so that the head 3 is supported by the seat portion 52 to allow the head 3 to pivot in the seat portion 52 similar to a ball and socket joint. The seat portion 52 further is in communication with the bore 51, and has an opening 52b through which the shank 2 of the bone anchoring element 1 can extend. An inner diameter of the seat portion 52 at the transition to the bore 51 is greater than an outer diameter of the head 3 and smaller than the inner diameter of the bore 51, such that an edge portion 52a is formed between the bore 51 and the seat portion 52. An internal thread 54 is provided at the receiving part 5 adjacent the top end 5a for cooperating with the outer locking element 8 of the locking device 7.

The receiving part 5, as shown in the depicted embodiment, serves as a long head receiving part that has extended legs, and has, at a distance from the first end 5a, a predetermined breaking point 5c that permits breaking off of a portion between the first end 5a and the predetermined breaking point 5c. Such a long head receiving part may be used, for example, for minimally invasive surgery. It shall be noted that the receiving part may also be designed without a long head, where in such a case the first or top end may be located approximately at the predetermined breaking point 5c.

In a lower portion of the receiving part 5, an inclined lower surface 5d is formed, for example, by cutting away a portion of the receiving part 5, to permit the anchoring element 1 to pivot at a larger angle to one side relative to the receiving part 5. Instead of an inclined lower end, the receiving part may alternatively be designed with a symmetrical lower end that permits symmetric angulation in all directions.

In the seat portion 52, a plurality of circumferentially distinct recesses 55 are provided. The recesses 55 are substantially spherical-segment shaped, with a radius considerably smaller than the radius of the seat portion 52. For example, as shown in the embodiment, four recesses 55 are formed in the seat portion 52, and are arranged in a circumferential direction near ends of a U-shaped recess 53 and at both sides therefrom, seen from a direction of the rod axis. The recesses 55 locally enlarge the diameter of the seat portion, and serve for providing an accommodation space for portions of the pressure element 6, described further below.

The pressure element 6 is formed in one piece. It is of a substantially cylindrical construction and has an outer diameter which allows it to move in an axial direction in the bore 51 of the receiving part 5. The pressure element 6 has a top end 6a and a bottom end 6b. At the top end 6a, a substantially U-shaped recess 61 is provided which is configured to receive the rod 100 therein. The depth of the recess 61 may be greater than the diameter of the rod 100, such that the free legs formed by the recess 61 extend above the surface of the rod 100 when the rod 100 is inserted.

At the bottom end 6b, a spherical recess 62 is provided for receiving the head 3 therein. A radius of the spherical recess 62 is slightly larger than the radius of the head 3 so that the head 3 fits easily into the recess 62. At the bottom end 6b, there are four cut-outs spaced substantially equidistantly in a circumferential direction, whereby four lugs, or projections, 63 are provided. The lugs 63 have an approximate V-shape when seen from a side view, for example, in FIG. 11a, where the free ends may be flat or rounded. However, an outer contour of the lugs 63 is not restricted to the shape shown in the embodiment. For example, the lugs can be rectangular or U-shaped, or otherwise shaped. The lugs 63 are arranged to the left side and the right side of the U-shaped recess 61 near ends of the recess 61 corresponding to the locations of the recesses 55 in the receiving part 5. A length of the lugs 63 and a depth of the spherical recess 62 is such that the lugs 63 extend beyond the area with the largest outer diameter E of the spherical head 3 when the pressure element 6 is mounted onto the head 3. Referring in particular to FIG. 11b, the lugs 63 each have a first section 63a adjacent the spherical recess 62 and a second section 63b extending from the first section 63a to the free end of the lug. An inner diameter D1 of the first spherical section 63a is the same as or is greater than the outer diameter of the spherical outer surface portion of the head 3 that comes into contact therewith. The inner diameter D2 of the second spherical portion 63b is slightly smaller than the largest outer diameter E of the spherical surface portion of the head 3. For example, diameter D2 is approximately 1% to 2% smaller than diameter D1, so that the pressure element 6 has a slight undersize with respect to the head 3 in the region of the second spherical portion 63b of the lugs 63. The undersize is present before the pressure element 6 is placed onto the head 3. The amount of the undersize may depend on the actual dimensions and also on the materials used for the respective parts. When the pressure element 6 is placed onto the head 3, the head 3 has to pass the second spherical portions 63b to move into the spherical recess 62, thereby slightly expanding the second spherical portions 63b. Hence, the pressure element 6 is configured to hold the head 3 by frictional forces exerted by the lugs 63 onto the head. 3. The strength of the frictional forces can be adjusted by designing the size of the lugs 63, in particular, the second spherical portions 63b, in an appropriate manner.

Furthermore, the pressure element 6 has a coaxial bore 64 for allowing access to the head 3 of the bone anchoring element with a tool.

All parts of the bone anchoring device are made of a body-compatible material, such as a body-compatible metal, for example, titanium, of body-compatible metal alloys, such as, for example, Nitinol, or of a body-compatible plastic material, such as, for example, polyetheretherketone (PEEK) or of combinations of these materials. The parts can be made of the same or of different materials.

Figure 15:
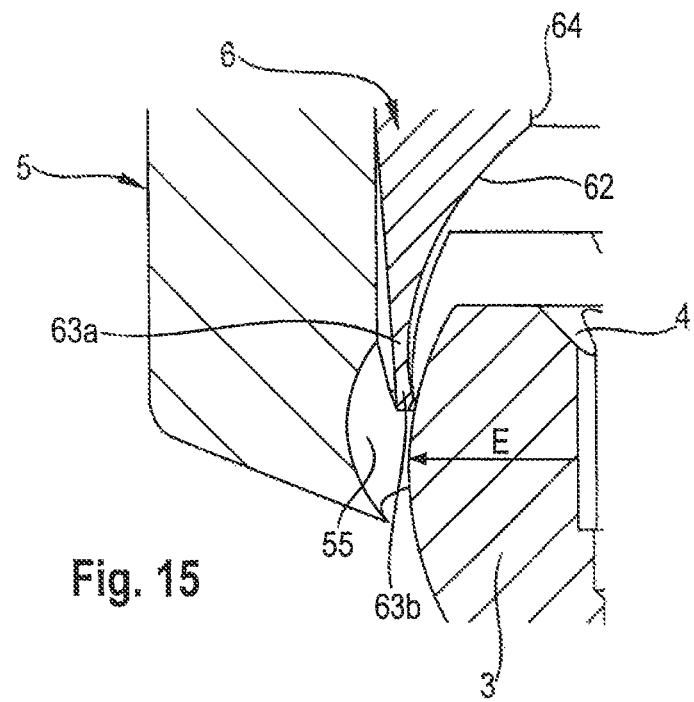
FIG. 15 shows an enlarged cross-sectional view of a portion of the bone anchoring device of FIGS. 1 and 2, with the pressure element not yet exerting pressure onto the head.
Figure 16:
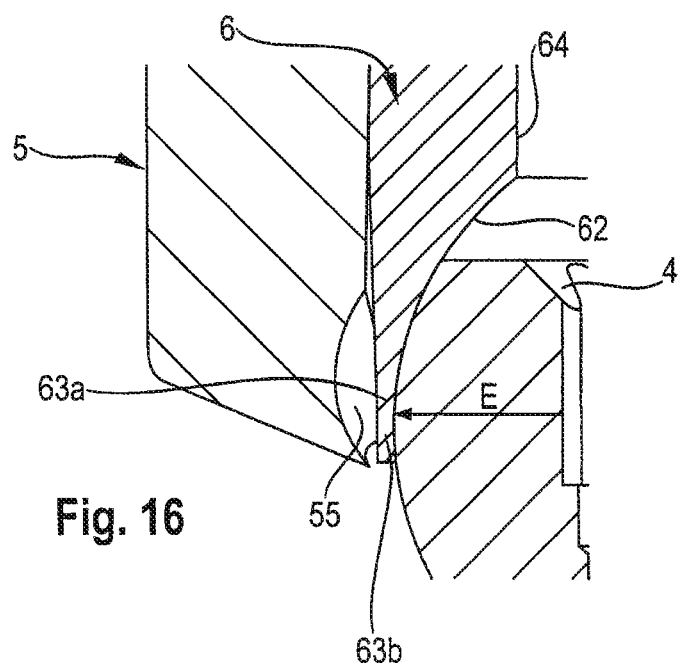
FIG. 16 shows an enlarged cross-sectional view of a portion of the bone anchoring device of FIGS. 1 and 2, with the pressure element exerting pressure onto the head.

The bone anchoring device may be used in a pre-assembled condition. In the pre-assembled condition, the head 3 of the bone anchoring element 1 is held in the seat 52 such that the head can pivot within the seat 52 and the shank 2 extends through the lower opening 52b. The pressure element 6 can be placed on the head 3 as shown in FIGS. 15 and 16. First, as shown in FIG. 15, the pressure element 6 is aligned with the receiving part 5, such that the U-shaped recesses 53 and 61 are aligned. Here, the lugs 63 may be aligned with the circumferential locations of the recesses 55 in the seat portion 52. The pressure element 6 is then shifted towards the bottom end 5b of the receiving part 5, such that the second spherical portions 63b of the lugs 63 are pressed over the spherical surface portion including the largest diameter E of the head 3. Thereby, the lugs 63 are spread slightly outward until the head 3 fits into the spherical recess 62 and the first spherical surface portion 63a of the lugs 63. The recesses 55 provide space for the spreading of the lugs 63. The lugs 63 do not engage the wall of the recesses 55, so that jamming of the pressure element within the receiving part 5 does not occur.

As depicted in FIG. 16, the head 3 contacts the spherical recess 62 and the lugs 63 over a certain contact area. In a region including the largest outer diameter E of the head 3, the lugs 63 exert a preload onto the head 3, so that the head 3 is clamped by frictional forces exerted by the lugs 63. The pressure element 6 may be preliminarily held in this position, for example, by crimping through crimp bores 70, shown in FIG. 3.

In use, at least two bone anchoring devices are anchored into bone parts or vertebrae. Then the receiving parts 5 are aligned to have a correct or desired orientation for insertion of the rod 100. Because the heads are temporarily clamped relative to the receiving parts 5 for pivoting, a force can be applied, for example manually, to overcome the clamping force until each receiving part 5 has the correct or desired orientation. When all of the receiving parts 5 are aligned, the rod 100 is inserted and the locking devices 7 are tightened. With the outer locking element 8, pressure may only be exerted onto the pressure element 6 at the top end 6a, such that the angular positions of the heads 3 can be locked. With the inner locking element 9 that exerts pressure only onto the rod 100, the rod can then be fixed.

Various modifications of the embodiments described above also are possible. For example, a number and location of the lugs may vary. Other means for preliminarily fixing or holding of the pressure element within the receiving part are also conceivable. For example, instead of crimping, the receiving part may be held by engagement portions of the receiving part and/or the pressure element that prevents escaping of the pressure element through the top end of the receiving part.

For the anchoring element, various different kinds of anchoring elements can also be used and combined with the receiving part. Such anchoring element may include, for example, screws with different lengths, with different diameters, cannulated screws, screws with different thread forms, nails, etc. In some embodiments, the head and the shaft can also be separate parts that are connectable to each other.

Various kinds of receiving parts can also be used, for example, parts with different locking devices. For example, instead of the two-part locking device, a one part locking device such as an inner screw which locks the rod and the head simultaneously can instead be used. Further, outer nuts, outer caps, bayonet locking devices, or various other locking devices can also be used. The recesses 55 may also have various other shapes, for example, a rectangular or a U-shape.

In a further modification, the receiving part may be configured to allow introduction of the bone anchoring element from the bottom end.

While the present invention has been described in connection with certain exemplary embodiments, it is to be understood that the invention is not limited to the disclosed embodiments, but is instead intended to cover various modifications and equivalent arrangements included within the spirit and scope of the appended claims, and equivalents thereof.

What is claimed is:

1. A polyaxial bone anchoring device comprising:
an anchoring element having a shank for anchoring to a bone and a head having an outer surface portion shaped as a segment of a sphere including a largest outer diameter of the sphere;
a receiving part having a first end and a second end, a channel for receiving a rod therein, a bore extending from the first end in a direction of the second end along a bore axis, a seat portion at the second end configured to contact the head, and at least one accommodation space in the seat portion; and
a pressure element having a head contacting surface portion comprising a plurality of circumferentially distinct projections and defining a recess having a first region configured to receive the head and a second region defined by portions of the projections and having a diameter smaller than the largest outer diameter of the sphere such that, when the head is held in the recess, the projections extend over a portion of the head with the largest outer diameter of the sphere,
wherein when the head contacts the seat portion, the pressure element is movable from a first position, wherein free ends of the projections are located at the largest diameter of the sphere and project radially into the at least one accommodation space, to a second position, wherein the free ends of the projections extend past the largest diameter of the sphere and project radially to a less degree toward or into the at least one accommodation space than in the first position and the second region of the head contacting surface portion is expanded from a neutral position to clamp the head by friction such that the clamped head remains pivotable with respect to the receiving part prior to being fixed.

2. The polyaxial bone anchoring device of claim 1, wherein the receiving part has a plurality of accommodation spaces.

3. The polyaxial bone anchoring device of claim 2, wherein each of the accommodation spaces is spherical-segment shaped.

4. The polyaxial bone anchoring device of claim 2, wherein a number of the accommodation spaces corresponds to a number of the projections.

5. The polyaxial bone anchoring device of claim 2, wherein the pressure element has a rod receiving channel, and wherein each of the projections is configured to be aligned with a corresponding one of the accommodation spaces when the channels of the receiving part and the pressure element are aligned with one another.

6. The polyaxial bone anchoring device of claim 1, wherein each of the projections has a portion in the first region and a portion in the second region,
wherein a first diameter defined by the portions of the projections in the first region is the same as or greater than a diameter of a portion of the head to be received in the first region, and a second diameter defined by the portions of the projections in the second region is smaller than the first diameter, and
wherein when the head is held in the recess, the portions of the projections defined by to the second region extend past the portion of the head with the largest outer diameter.

7. The polyaxial bone anchoring device of claim 1, wherein the pressure element is substantially cylindrical, with a first end and a second end, and wherein the recess includes a spherical-segment shaped portion at the second end of the pressure element and is configured to face the head.

8. The polyaxial bone anchoring device of claim 1, wherein a portion of the head contacting surface portion excluding the projections has an inner surface defining a recess that is the same or is slightly larger than the shape of the head.

9. The polyaxial bone anchoring device of claim 1, wherein a distance between a wall of the accommodation space and the bore axis is greater than a radial distance from a central axis of the pressure element to an outer surface of the projections.

10. The polyaxial bone anchoring device of claim 1, wherein, in the second position, the projections are entirely outside the at least one accommodation space.

11. The polyaxial bone anchoring device of claim 1, wherein at least two of the projections are configured to clamp the head from opposite sides.

12. The polyaxial bone anchoring device of claim 1, wherein at least three of the projections are spaced equidistantly from one another in a circumferential direction on the pressure element.

13. The polyaxial bone anchoring device of claim 1, wherein each of the projections has a substantially V-shaped contour that narrows towards the free end of the projection.

14. The polyaxial bone anchoring device of claim 1, wherein the seat portion has a spherical-segment shaped region.

15. The polyaxial bone anchoring device of claim 1, further comprising a locking device configured to cooperate with the receiving part to lock the head in the seat portion and to fix a rod in the channel.

16. The polyaxial bone anchoring device of claim 1, wherein, in the first and second positions, the free ends of the projections remain spaced apart from the receiving part.

17. The polyaxial bone anchoring device of claim 1, wherein when the head is held in the recess, the projections contact a portion of the head below the largest outer diameter of the sphere.

18. A method for coupling a rod to a bone via a polyaxial bone anchoring device, the bone anchoring device comprising; an anchoring element having a shank for anchoring in a bone and a head having an outer surface portion shaped as a segment of a sphere including a largest outer diameter of the sphere, a receiving part having a first end and a second end, a channel for receiving the rod therein, a bore extending from the first end in a direction of the second end along a bore axis, a seat portion at the second end configured to contact the head, and at least one accommodation space in the seat portion, and a pressure element having a head contacting surface portion comprising a plurality of circumferentially distinct projections and defining a recess having a first region configured to receive the head and a second region defined by portions of the projections and having a diameter smaller than the largest outer diameter of the sphere such that, when the head is held in the recess, the projections extend over a portion of the head with the largest outer diameter of the sphere and contact a portion of the head below the largest outer diameter of the sphere, the method comprising:

attaching the pressure element to the head of the anchoring element when the head is in the receiving part and contacting the seat portion such that, in a first position wherein free ends of the projections are located at the largest diameter of the sphere, the free ends of the projections project radially into the at least one accommodation space, and in a second position wherein the free ends of the projections extend past the largest diameter of the sphere, the free ends of the projections project radially to a less degree toward or into the at least one accommodation space than in the first position and the second region of the head contacting surface portion is expanded from a neutral position to clamp the head by friction to hold the head at a temporary angular position relative to the receiving part by the friction;

inserting the anchoring element into a bone when the head and the pressure element are in the receiving part and the pressure element is holding the head in the recess;

applying a force greater than the friction on the anchoring element or the receiving part to pivot the receiving part and change the angular position of the head relative to the receiving part;

inserting the rod into the channel of the receiving part; and advancing a locking device in the channel of the receiving part to advance the rod and the pressure element towards the second end of the receiving part to exert further pressure onto the head for locking the angular position of the head relative to the receiving part and to lock a position of the rod relative to the anchoring element.

19. The method of claim 18, wherein in the second position, the projections are entirely outside the at least one accommodation space.

20. The method of claim 18, wherein the locking device comprises an outer locking element and an inner locking element, wherein the outer locking element advances the pressure element to lock the angular position of the head relative to the receiving part, and the inner locking element locks the position of the rod relative to the anchoring element.

21. A polyaxial bone anchoring device comprising:

an anchoring element having a shank for anchoring to a bone and a head having an outer surface portion shaped as a segment of a sphere including a largest outer diameter of the sphere;

a receiving part having a first end and a second end, a channel for receiving a rod therein, a bore extending from the first end in a direction of the second end along a bore axis, and a seat portion at the second end for receiving the head; and a pressure element having a head contacting surface portion comprising a plurality of circumferentially distinct projections and defining a recess having a first region configured to receive the head and a second region defined by portions of the projections, the second region of the recess having an undersize compared to the shape of the head such that, when the head is held in the recess, the projections extend over a portion of the head with the largest outer diameter and the head contacting surface portion corresponding to the second region is expanded from a neutral position to clamp the head by friction;

wherein when the pressure element is in the neutral position, the first region of the recess is a recessed spherical-segment shape with a first diameter that is the same size as or larger than a portion of the head to be received in the first region of the recess, and the second region of the recess is a recessed spherical-segment shape with a second diameter smaller than the first diameter and smaller than a portion of the head to be received in the second region of the recess; and wherein when the head and the pressure element are in the receiving part and the pressure element is holding the head in the recess, the head is pivotable with respect to the receiving part and can be fixed at an angle by exerting further pressure via the pressure element onto the head.

* * * * *